US00PP37073P2

(12) United States Plant Patent
Jhe

(10) Patent No.: US PP37,073 P2
(45) Date of Patent: Oct. 28, 2025

(54) ***EPIPREMNUM* PLANT NAMED 'Cla20241218'**

(50) Latin Name: *Epipremnum pinnatum*
Varietal Denomination: Cla20241218

(71) Applicant: Flores Laeti, Den Hoorn (NL)

(72) Inventor: Chen Shih Jhe, Linluo Township (TW)

(73) Assignee: Flores Laeti BV (NL)

( * ) Notice: Subject to any disclaimer, the term of this patent is extended or adjusted under 35 U.S.C. 154(b) by 0 days.

(21) Appl. No.: 18/991,825

(22) Filed: Dec. 23, 2024

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

PUBLICATIONS

Cashmear website for *epipremnum pinnatum* vs *Epipremnum*. 2022. https://cashmear.ca/blogs/horticulture-2/epipremnum-pinnatum-vs-aureum (Year: 2022).*

* cited by examiner

*Primary Examiner* — Karen M Redden

(57) ABSTRACT

A new and distinct cultivar of *Epipremnum* plant named 'Cla20241218' is disclosed, characterized by small cordate to broad elliptic variegated leaves with three different colors (Creamy white, Light green and dark Green). The green variegation varies in shape, size and distribution on the leaf surface. Foliage is uniquely fenestrated. Plants are Compact and dense growth with short internodes. The new cultivar is an *Epipremnum*, normally used for indoor ornamental purposes.

3 Drawing Sheets

Latin name of the genus and species: *Epipremnum pinnatum.*

Cultivar denomination: 'Cla20241218'.

BACKGROUND OF THE INVENTION

The new *Epipremnum* cultivar is the result of a naturally occurring whole plant mutation of *Epipremnum pinnatum* 'Marble Queen', unpatented. *Epipremnum* 'Cla20241218' was found and selected by the inventor in a nursery in Pingtung County, Taiwan in November of 2022.

Asexual reproduction of the new cultivar has been performed by vegetative cuttings. This was first performed at the same nursery in Pingtung County, Taiwan in December of 2022, and has shown that the unique features of this cultivar are stable and reproduced true to type in multiple successive generations.

SUMMARY OF THE INVENTION

The cultivar 'Cla20241218' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Cla20241218'. These characteristics in combination distinguish 'Cla20241218' as a new and distinct *Epipremnum* cultivar:

1. Small cordate to broad elliptic variegated leaves with three different colors (Creamy white, Light green and dark Green).

2. Unique variegated fenestrated leaves. Fenestration appears at an early stage, in the newest growth of the plant and continues in mature plants.
3. Compact and dense growth with short internodes.
4. Clear, distinct variegation pattern.
5. Varying shape and size of green variegation distributed on the leaf surface.

PARENT COMPARISON

Plants of the new cultivar *Epipremnum* 'Cla20241218' are similar to plants of *Epipremnum* 'Marble Queen' in most horticultural characteristics; however, plants of the new cultivar 'Cla20241218' differ in the following:

1. The new cultivar has unique fenestrated leaves, which 'Marble Queen' doesn't have.
2. The new cultivar has more creamy white in its leaves. 'Marble Queen' has in general about 50% green and 50% creamy white color
3. The new cultivar has many shades of green within its variegation, while 'Marble Queen' has no more than 2 shades of green
4. The new cultivar has smaller leaves and shorter leaf internodes.

COMMERCIAL COMPARISON

Plants of the new cultivar 'Cla20241218' are comparable to the commercial cultivar *Epipremnum* 'Snow Queen', unpatented. The two *Epipremnum* varieties are similar in most horticultural characteristics, however, the new cultivar 'Cla20241218' differs in the following:

1. 'Snow Queen' doesn't have unique fenestrated leaves.

2. 'Snow Queen' has more cream variegation than the new cultivar. 'Snow Queen' has about 80% cream variegation and 20% green
3. Snow Queen' has more acute foliage than the new cultivar.
4. 'Snow Queen' has more irregular, random splashes of green pattern than the new cultivar.

Plants of the new cultivar 'Cla20241218' are comparable to the commercial cultivar *Epipremnum* 'Marble', unpatented. The two *Epipremnum* varieties are similar in most horticultural characteristics, however, the new cultivar 'Cla20241218' differs in the following;

1. 'Cla20241218' produces split and fenestrated leaves at an earlier stage than 'Marble'. Fenestration in the new cultivar can appear in the earliest growth and does not appear in 'Marble' until the plant begins producing stringers
2. 'Cla20241218' consistently has more creamy white and light green variegation than 'Marble'. 'Marble' has at least 50% green coverage of the leaf.
3. 'Marble' has longer internodes and a less dense center than the new cultivar, resulting in a more stretched plant.

BRIEF DESCRIPTION OF THE PHOTOGRAPHS

The accompanying photograph in FIG. 1 illustrates in full color a typical plant of the new cultivar, 'Cla20241218' grown in a greenhouse in Pingtung County, Taiwan. The plant is approximately 12 weeks old in a 9 cm pot.

Figure 1:
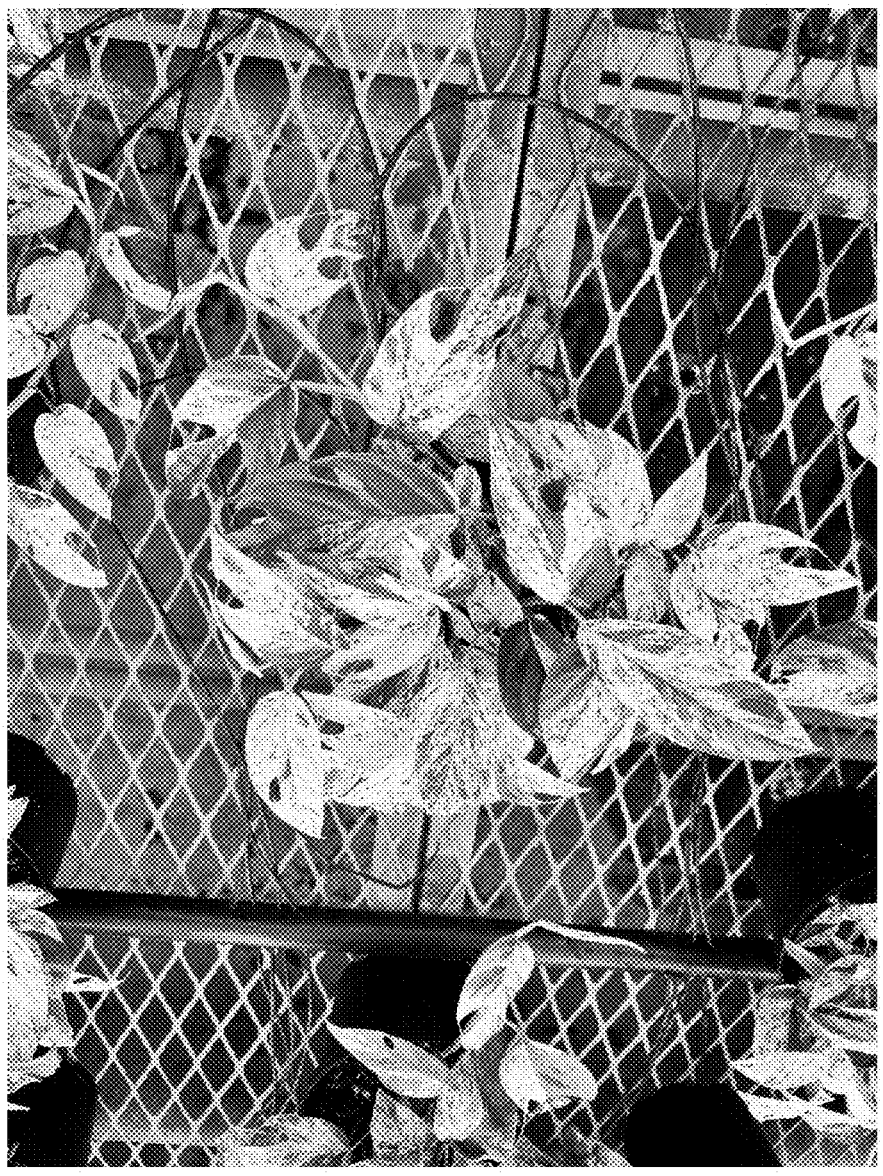
Figure 2:
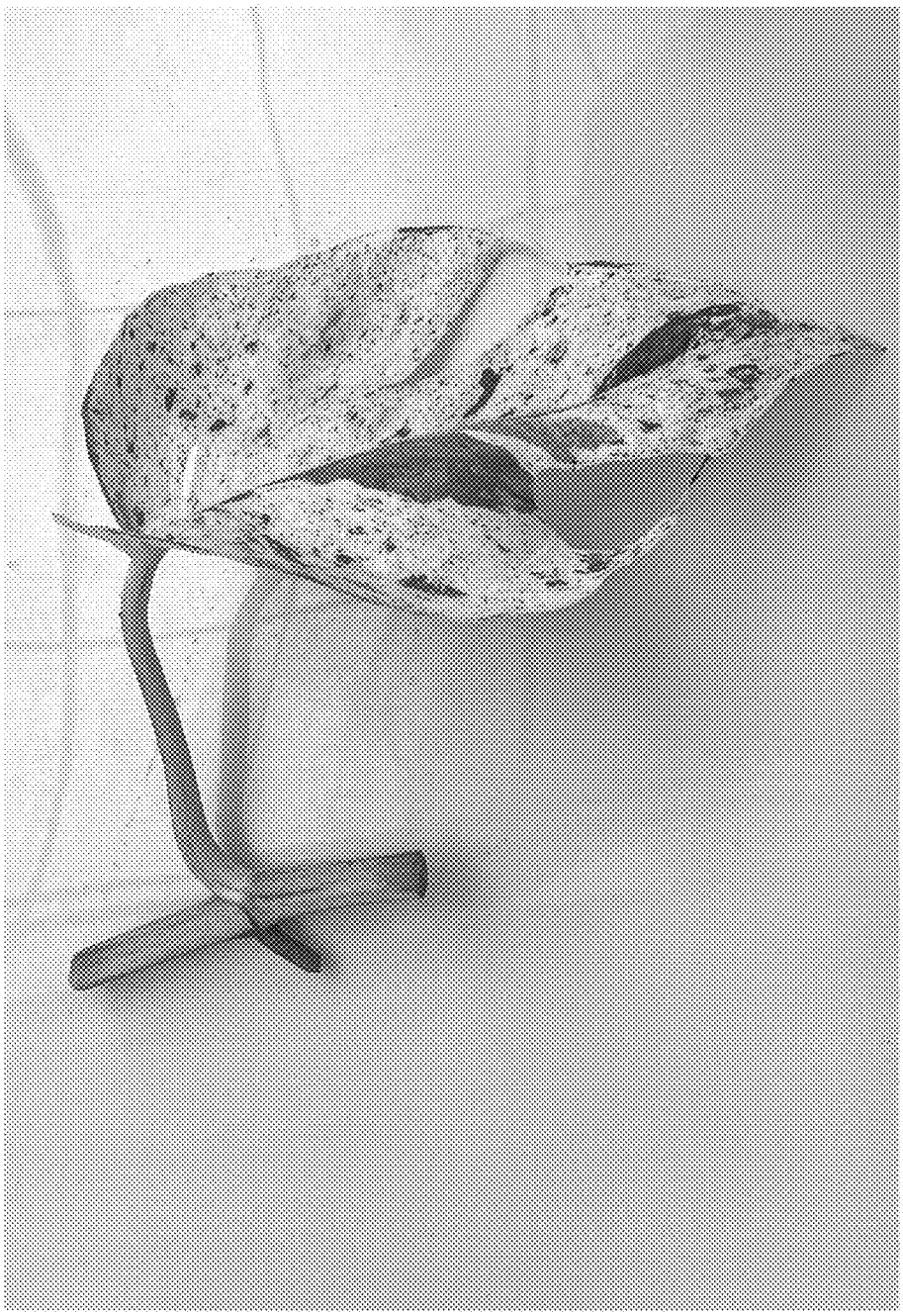
FIG. 2 illustrates a close-up view of a fenestrated leaf in the cutting stage.
Figure 3:
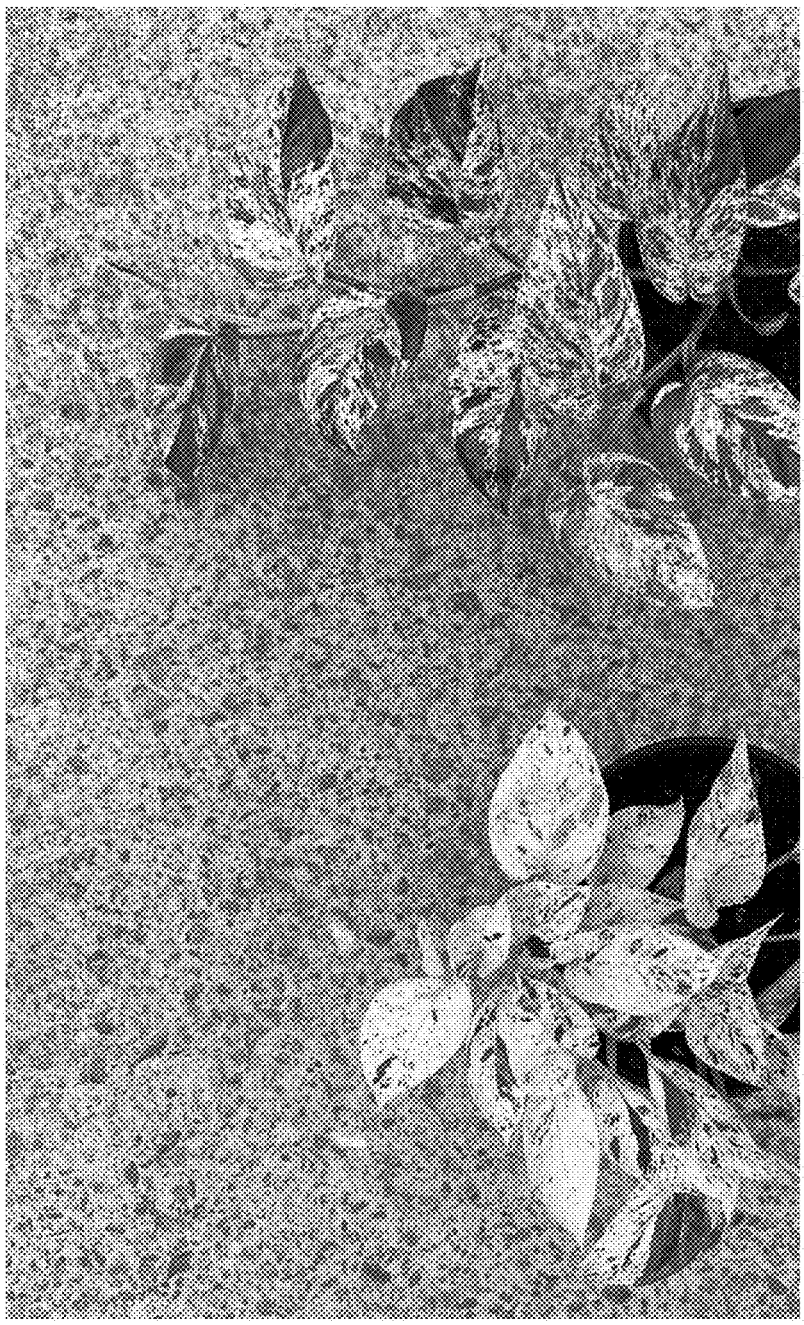
FIG. 3 is a photograph comparing a plant of 'Cla20241218' (left side) with a plant of the comparator 'Marble' (right side).

These plants were grown under identical conditions in Pingtung County, Taiwan. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'Cla20241218' plants grown in a greenhouse in Nipomo, California The growing temperature ranged from approximately 20° C. to 25° C. during the day and from approximately 18° C. to 20° C. during the night. General light conditions are normal sunlight and numerical values represent averages of typical plant types.

Botanical classification: *Epipremnum pinnatum* 'Cla20241218'.

PROPAGATION

Type of propagation typically used: Terminal vegetative cuttings.

Time to initiate roots: About 14 days at approximately 25° C.

Time to produce a rooted plantlet: About 3 weeks at approximately 22° C. to 28° C.

Root description: Primary roots fleshy, about 7 to 9 mm in diameter colored near Greyed-White 157A.

PLANT

Age of plant described: 10 weeks old from a rooted cutting.

Container size: 6-inch pot.

Plant shape: Prostrate creeper or climber with support and training.

Height: Approximately 10 to 12 cm to top of highest leaf.

Plant spread: Approximately 32 cm in a 6-inch pot.

Normal commercial pot size: 4, 6, 8 inch pots.

Growth rate: Moderate to nearly rapid.

Branching characteristics: 2 to 4 lateral emerge from a pinch. Lateral ranches usually not occurring unless pinched.

Branch description:

*Average length* (*excluding petiole*).—Average range 12 to 22 cm on a plant of this age.

*Average width*.—5 to 6 mm.

*Shape*.—Round with ridges.

*Texture*.—Glabrous.

*Color*.—Yellow-Green 145D striped Green 143C and 137D.

FOLIAGE

Leaf:

*Arrangement*.—Sub-alternate, occurring only top surfaces of branch.

*Leaf Internode*.—3 to 4 cm.

*Average length* (*excluding petiole*).—Average range 8 to 12 cm.

*Average width*.—Average range 4 to 5.5 cm.

*Shape of blade*.—Cordate to broad elliptic. Distinctly fenestrate on about 20 to 30% of leaves. Usually one fenestration present, rarely 2. Fenestration is irregularly oblong, 7 to 18 cm in diameter and 15 to 30 mm long.

*Aspect*.—Flat to slightly undulate.

*Apex*.—Acute.

*Base*.—Hastate

*Margin*.—Entire.

*Texture of top surface*.—Glabrous.

*Texture of bottom surface*.—Glabrous.

*Color*.—Young foliage upper side: Near R.H.S. White N155D. Speckles and blotches near Green 137C, 137D, 138A, 138B and 143C. Colors both marbled together and solidly blotched. Green color makes up approximately 20% of surface. Young foliage under side: Near R.H.S. White N155D. Speckles and blotches near Green 137D, 138B, 138C and 143C. Colors both marbled together and solidly blotched. Green color makes up approximately 20% of surface. Mature foliage upper side: Near R.H.S. White N155D. Speckles and blotches near Green 137C, 137D, 138A, 138B and 143C. Colors both marbled together and solidly blotched. Green color makes up approximately 30% to 40% of surface. Mature foliage under side: Near R.H.S. White N155D. Speckles and blotches near Green 137D, 138B, 138C and 143C. Colors both marbled together and solidly blotched. Green color makes up approximately 20% of surface.

Venation:

*Type*.—Pinnate.

*Venation coloration upper side*.—Indistinguishable from leaf blade.

*Venation coloration under side*.—Main vein Green-White 157B. Lateral veins indistinguishable from leaf blade.

Petiole:

*Length*.—Average range 3.3 to 4.4 cm.

*Width*.—At geniculum: Approximately 6 mm. Above geniculum: Approximately 4 mm.

*Texture*.—Glabrous.

*Color*.—Near RHS Green-White 157A striped Green 143C and 137D.

*Strength*.—Moderate, flexible.

FLOWER

Not observed to date.

REPRODUCTIVE ORGANS

Not observed to date.

OTHER CHARACTERISTICS

Fruits and seeds: Not observed to date.

Disease/pest resistance: Neither resistance nor susceptibility to other normal diseases and pests of *Epipremnum* observed.

Temperature range: About 5° C. to 40° C.

What is claimed is:

1. A new and distinct cultivar of *Epipremnum* plant named 'Cla20241218' as herein illustrated and described.

* * * * *